US010265042B2

(12) United States Patent
Stoutenburgh et al.

(10) Patent No.: US 10,265,042 B2
(45) Date of Patent: Apr. 23, 2019

(54) RADIOLOGICAL IMAGING DEVICE WITH IMPROVED FUNCTIONING

(71) Applicant: Epica International, Inc., San Clemente, CA (US)

(72) Inventors: Gregory William Stoutenburgh, San Clemente, CA (US); Damiano Fortuna, Rignano Sull'Arno (IT); Leonardo Manetti, Montevarchi (IT)

(73) Assignee: Epica International, Inc., San Clemente, CA (US)

( * ) Notice: Subject to any disclaimer, the term of this patent is extended or adjusted under 35 U.S.C. 154(b) by 0 days.

(21) Appl. No.: 14/323,861

(22) Filed: Jul. 3, 2014

(65) Prior Publication Data

US 2015/0208993 A1    Jul. 30, 2015

Related U.S. Application Data

(60) Provisional application No. 61/932,024, filed on Jan. 27, 2014, provisional application No. 61/932,028, (Continued)

(51) Int. Cl.
*A61B 6/00* (2006.01)
*A61B 6/03* (2006.01)
(Continued)

(52) U.S. Cl.
CPC ............ *A61B 6/5205* (2013.01); *A61B 6/032* (2013.01); *A61B 6/035* (2013.01); *A61B 6/0407* (2013.01);
(Continued)

(58) Field of Classification Search
CPC ....... A61B 6/032; A61B 6/4233; A61B 6/037; A61B 6/035; A61B 6/487; A61B 6/42;
(Continued)

(56) References Cited

U.S. PATENT DOCUMENTS

| 6,072,851 A * | 6/2000 | Sivers ..................... A61B 6/032 378/15 |
| 6,114,701 A | 9/2000 | Plummer et al. |

(Continued)

OTHER PUBLICATIONS

International Search Report dated Jun. 10, 2015 in corresponding PCT Application No. PCT/US2015/011625 filed Jan. 15, 2015, inventor, Stoutenburgh, Gregory W.
(Continued)

*Primary Examiner* — Chih-Cheng Kao
(74) *Attorney, Agent, or Firm* — Steptoe & Johnson LLP

(57) ABSTRACT

A radiological imaging device that includes a source that emits radiation that passes through at least part of a patient, the radiation defining a central axis of propagation; and a receiving device that receives the radiation and is arranged on the opposite side of the patient with respect to the source. The receiving device includes a first detector to detect radiation when performing at least one of tomography and fluoroscopy, a second detector to detect radiation when performing at least one of radiography and tomography; and a movement apparatus arranged to displace the first and second detectors with respect to the source. The movement apparatus provides a first active configuration in which the radiation hits the first detector and a second active configuration in which the radiation hits the second detector.

7 Claims, 10 Drawing Sheets

Related U.S. Application Data filed on Jan. 27, 2014, provisional application No. 61/932,034, filed on Jan. 27, 2014, provisional application No. 61/944,956, filed on Feb. 26, 2014.

(51) Int. Cl.
 *A61B 6/04* (2006.01)
 *A61B 6/06* (2006.01)
 *A61B 6/08* (2006.01)

(52) U.S. Cl.
 CPC .............. *A61B 6/06* (2013.01); *A61B 6/08* (2013.01); *A61B 6/4035* (2013.01); *A61B 6/4233* (2013.01); *A61B 6/487* (2013.01); *A61B 6/542* (2013.01)

(58) Field of Classification Search
 CPC ...... A61B 6/4266; A63H 17/00; A63H 17/26; F16H 1/22; F16H 3/001; F16H 57/033; Y10T 29/49716; Y10T 74/19074; Y10T 74/19605; Y10T 74/19614; Y10T 74/19642
 See application file for complete search history.

(56) References Cited

U.S. PATENT DOCUMENTS

| | | |
|---|---|---|
| 2002/0191734 A1 | 12/2002 | Kojima et al. |
| 2003/0002626 A1 | 1/2003 | Hoheisel et al. |
| 2004/0013225 A1* | 1/2004 | Gregerson ............. A61B 6/032 378/19 |
| 2004/0101095 A1* | 5/2004 | Jing .................... A61B 6/06 378/37 |
| 2006/0233301 A1* | 10/2006 | Erhardt ................. A61B 6/032 378/38 |
| 2007/0029510 A1 | 2/2007 | Hermann et al. |
| 2007/0183559 A1 | 8/2007 | Hempel |
| 2007/0189447 A1* | 8/2007 | Holler ................. A61B 6/4233 378/37 |
| 2008/0103391 A1 | 5/2008 | Dos Santos Varela |
| 2008/0181359 A1* | 7/2008 | Stayman ................ A61B 6/032 378/20 |
| 2008/0219403 A1 | 9/2008 | Moore |
| 2009/0116617 A1* | 5/2009 | Mastronardi ........ G01N 23/201 378/87 |
| 2009/0238427 A1* | 9/2009 | Hsieh ..................... A61B 6/032 382/131 |
| 2010/0074400 A1* | 3/2010 | Sendai ................. A61B 6/0435 378/37 |
| 2011/0080994 A1* | 4/2011 | Hoffman ............... A61B 6/032 378/19 |
| 2011/0152676 A1* | 6/2011 | Groszmann ............. A61B 6/12 600/426 |
| 2011/0249787 A1* | 10/2011 | Frey ........................ A61B 6/06 378/16 |
| 2011/0268245 A1 | 11/2011 | Eberhard |
| 2012/0014506 A1 | 1/2012 | Lee et al. |
| 2012/0170711 A1* | 7/2012 | Souchay ................. A61B 6/06 378/37 |
| 2012/0189096 A1 | 7/2012 | Erhardt et al. |
| 2012/0288056 A1* | 11/2012 | Murakoshi ........... A61B 6/4233 378/37 |
| 2012/0328072 A1 | 12/2012 | Shi et al. |
| 2013/0170627 A1 | 7/2013 | Topfer et al. |

OTHER PUBLICATIONS

Supplementary European Search Report dated Jan. 18, 2017 in corresponding European Application No. 15739834.8, inventor, Stoutenburgh, Gregory W.

\* cited by examiner

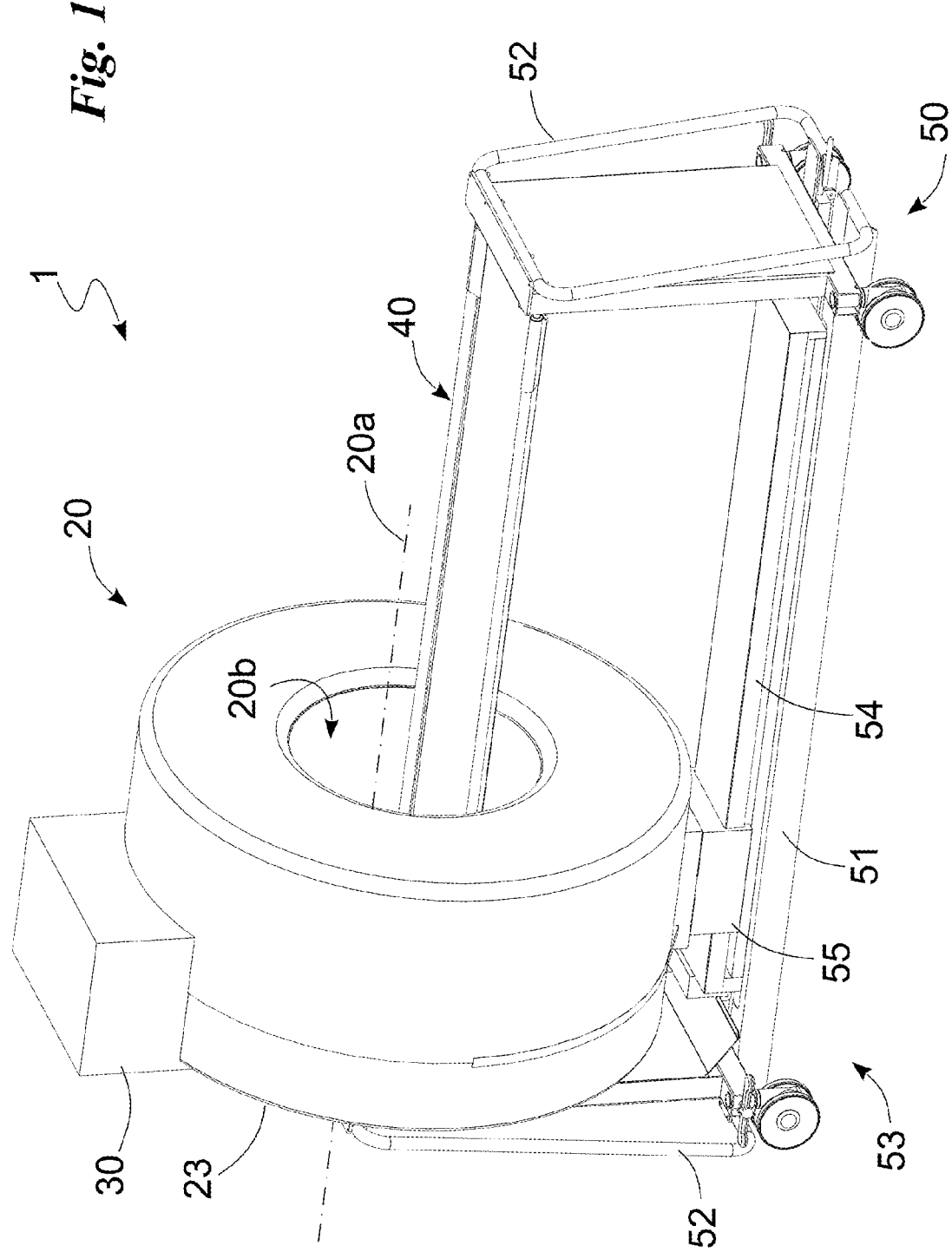

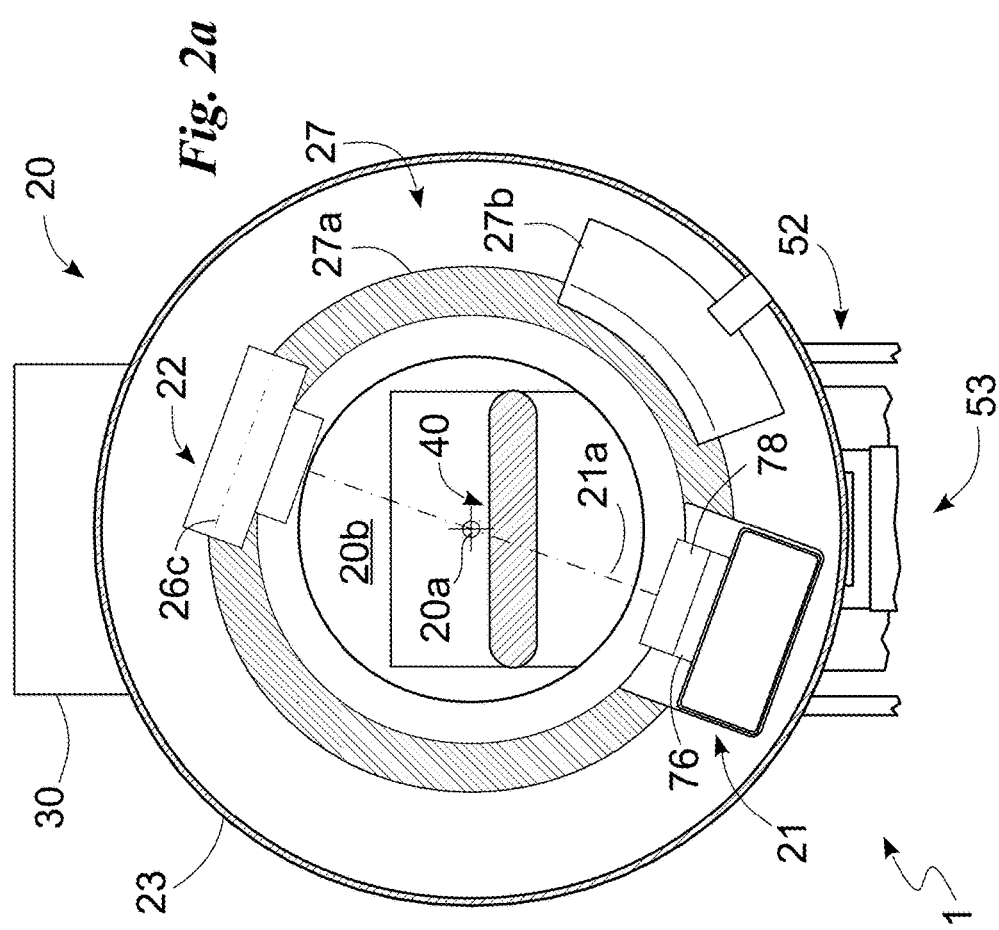

| Input Parameters | | | Output Configuration Paramaters | | | |
|---|---|---|---|---|---|---|
| Imaging Procedure | Tissue / Region of interest | Patient Size | kV | mA | ms | Filter |
| Tomography | Hard / Head | Any | 100 | 30 | 10 | 3 mm Al + 0.2 mm Cu |
| Tomography | Hard / Thorax | Any | 100 | 60 | 5 | 3 mm Al + 0.2 mm Cu |
| Tomography | Soft / Abdomen | Any | 60 | 60 | 10 | 2 mm Al |
| Tomography | Soft / Limbs | Any | 60 | 30 | 15 | 2 mm Al |
| Radiography | Head | Small | 70 | 20 | 10 | 2 mm Al |
| Radiography | Thorax | Small | 80 | 25 | 2 | 2 mm Al |
| Radiography | Abdomen | Small | 75 | 30 | 10 | 2 mm Al |
| Radiography | Limbs | Small | 45 | 30 | 15 | 2 mm Al |
| Radiography | Head | Medium | 80 | 30 | 20 | 2 mm Al |
| Radiography | Thorax | Medium | 85 | 30 | 2 | 2 mm Al |
| Radiography | Abdomen | Medium | 80 | 40 | 10 | 2 mm Al |
| Radiography | Limbs | Medium | 50 | 30 | 20 | 2 mm Al |
| Radiography | Head | Large | 85 | 30 | 20 | 2 mm Al |
| Radiography | Thorax | Large | 95 | 30 | 2 | 2 mm Al |
| Radiography | Abdomen | Large | 90 | 60 | 20 | 2 mm Al |
| Radiography | Limbs | Large | 55 | 30 | 20 | 2 mm Al |
| Fluoroscopy | Head | Small | 70 | 20 | 5 | 2 mm Al |
| Fluoroscopy | Thorax | Small | 80 | 25 | 2 | 2 mm Al |
| Fluoroscopy | Abdomen | Small | 75 | 30 | 5 | 2 mm Al |
| Fluoroscopy | Limbs | Small | 45 | 30 | 5 | 2 mm Al |
| Fluoroscopy | Head | Medium | 80 | 30 | 5 | 2 mm Al |
| Fluoroscopy | Thorax | Medium | 85 | 30 | 2 | 2 mm Al |
| Fluoroscopy | Abdomen | Medium | 80 | 40 | 5 | 2 mm Al |
| Fluoroscopy | Limbs | Medium | 50 | 30 | 5 | 2 mm Al |
| Fluoroscopy | Head | Large | 85 | 30 | 5 | 2 mm Al |
| Fluoroscopy | Thorax | Large | 95 | 30 | 2 | 2 mm Al |
| Fluoroscopy | Abdomen | Large | 90 | 60 | 5 | 2 mm Al |
| Fluoroscopy | Limbs | Large | 55 | 30 | 5 | 2 mm Al |

Fig. 2b

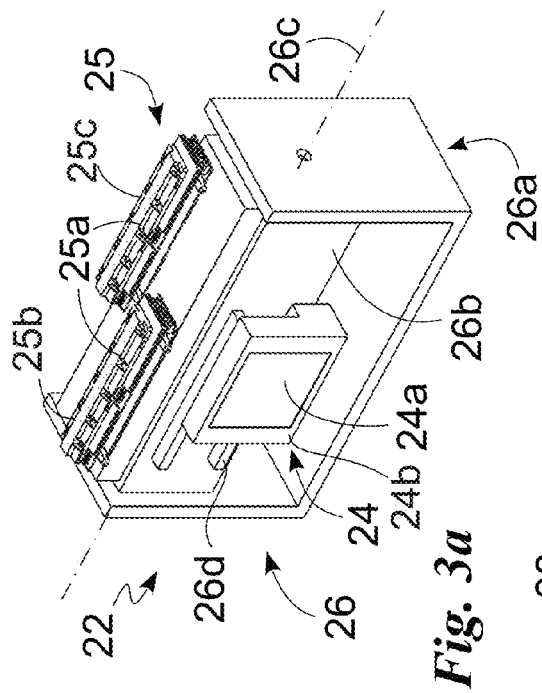
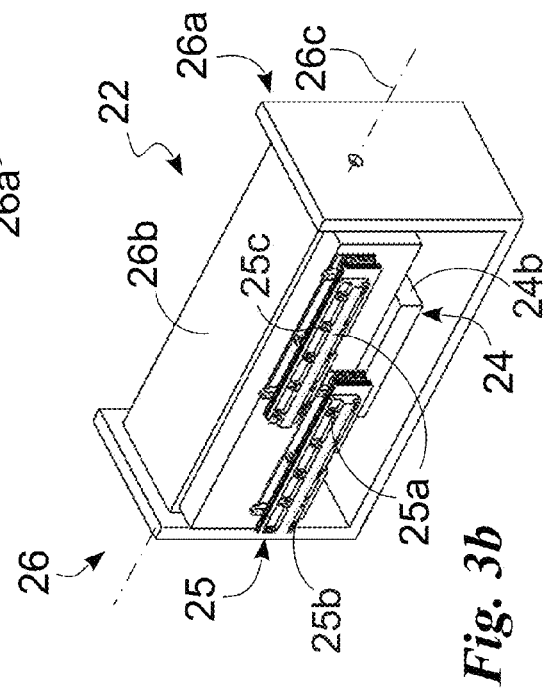
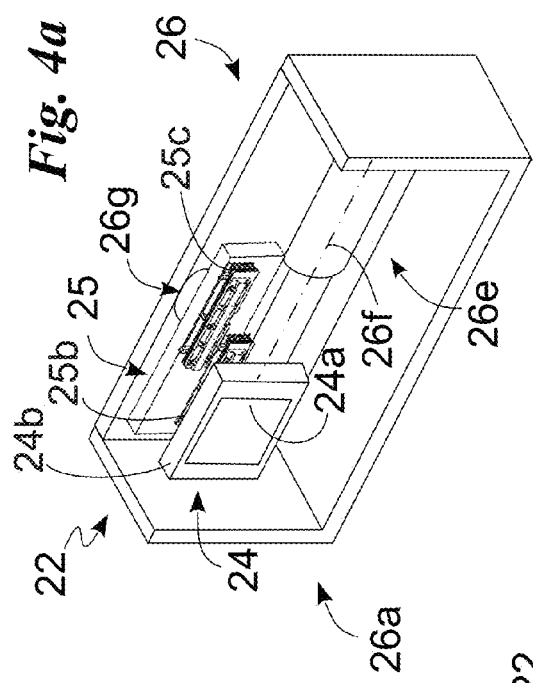
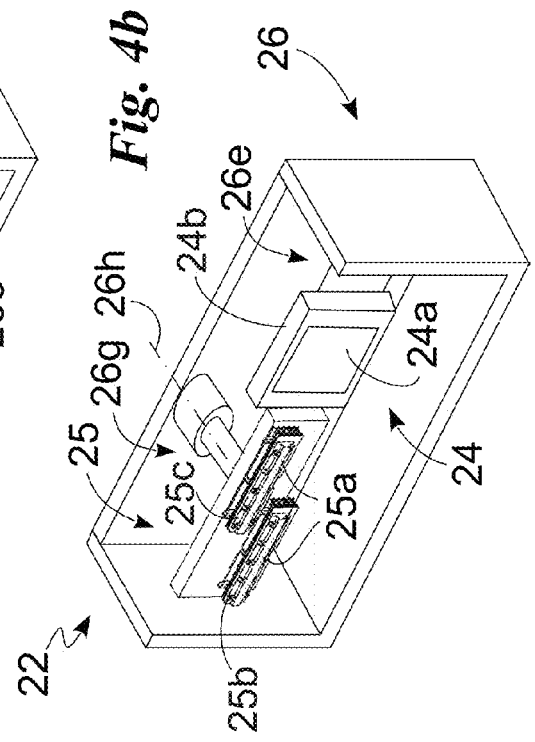

RADIOLOGICAL IMAGING DEVICE WITH IMPROVED FUNCTIONING

CROSS REFERENCE TO RELATED APPLICATIONS

This application claims priority to U.S. Provisional Patent Application Nos. 61/932,024, filed Jan. 27, 2014; 61/932,028, filed Jan. 27, 2014; 61/932,034, filed Jan. 27, 2014; and 61/944,956, filed Feb. 26, 2014, the contents of which are incorporated herein by reference in their entireties.

BACKGROUND OF THE INVENTION

Field

Example aspects herein relate generally to obtaining radiological images, and, more particularly, to a method, system, and apparatus for performing fluoroscopy, tomography, and radiography.

Description of Related Art

Many conventional imaging devices comprise a bed on which the patient lies, a control station suitable to control the functioning of the device; a gantry, that is, a device having a cavity in which the portion to be analyzed is inserted and suitable to perform the radiological imaging of the patient.

Inside the gantry, the radiological imaging devices are provided with a source suitable to emit X-rays, and a detector, that is an element suitable to receive the X-rays after these have traversed the portion to be analyzed. The type of detector utilized varies from one device to another according to the type of radiological imaging procedure performed by said device.

The prior art radiological imaging devices require a specific detector for each analysis (e.g., x-ray radiography, fluoroscopy, or computed tomography), which means each device can perform only one type of analysis. As a result, if a patient needs to undergo different analyses, the patient has to be moved from one device to another, which adds delay and risks to the patient's health. In the case in which a patient needs to undergo several analyses, the patient has to be taken from the radiological imaging device, placed on a bed so as to be moved, picked up again and then placed on a second radiological imaging device.

Additionally, in order to perform different types of analyses to a high standard, a medical center must be equipped with several radiological imaging devices, involving substantial outlays. In response, specific radiological devices have been developed in recent years that also use conventional flat panel sensors to perform two-dimensional radiographic imaging.

However, two-dimensional radiographic images obtained by conventional flat panel sensors typically are of poor quality as a result of diffused, so-called parasitic radiation, formed by the interactions between X-rays and matter, which hits the detector and spoils the quality of the image. Furthermore, owing to parasitic radiation, such devices may undesirably expose the patient and, in some cases, the operator, to high doses of radiation. This can be a concern in the field of veterinary radiology, as human operators are frequently required to hold the patient in position when performing a radiographic examination, and are thus susceptible to being exposed to parasitic radiation.

In order to reduce the incidence of parasitic radiation, conventional radiological imaging devices are often fitted with anti-diffusion grids composed of thin lead plates fixedly arranged parallel to each other so as to prevent the diffused rays from reaching the flat panel sensor. However, such grids are only partially effective in remedying the effects of parasitic radiation on image quality. Moreover, the presence of said anti-diffusion grids imposes the need to use a higher dose, thereby possibly increasing the danger of causing illness.

SUMMARY OF THE INVENTION

Existing limitations associated with the foregoing, as well as other limitations, can be overcome by a method for operating a radiological imaging device, and by a system, apparatus, and computer program that operates in accordance with the method.

According to one example embodiment herein, a radiological imaging device comprises a source that emits radiation that passes through at least part of a patient, the radiation defining a central axis of propagation; and a receiving device that receives the radiation and is arranged on the opposite side of the patient with respect to the source. The receiving device includes a first detector to detect radiation when performing at least one of tomography and fluoroscopy, and a second detector to detect radiation when performing at least one of radiography and tomography. The radiological imaging device also comprises a movement apparatus arranged to displace the first and second detectors with respect to the source, to provide a first active configuration in which the radiation hits the first detector and a second active configuration in which the radiation hits the second detector.

In one example embodiment herein, the first detector comprises at least one flat panel sensor and the second detector comprises at least one linear sensor. In a further example embodiment herein, in the first active configuration, the distance between the first detector and the source is substantially equal to the distance between the second detector and the source in the second active configuration.

In another example embodiment herein, the movement apparatus displaces the first and second detectors with respect to the source by means of a rotation about an axis of rotation. In a further example embodiment herein, the axis of rotation is substantially perpendicular to the central axis of propagation.

In another example embodiment herein, the movement apparatus changes between the first and second active configuration by means of a mutual translation of the first and second detectors. In a further example embodiment herein, the movement apparatus comprises a first linear actuator to move the first detector along a first direction of translation and a second linear actuator to move the second detector along a second direction of translation. In yet another example embodiment herein, the first direction of translation is substantially perpendicular to the central axis of propagation and the second direction of translation is substantially parallel to the central axis of propagation.

In an example embodiment herein, the movement apparatus changes the active configuration by means of a translation of the first detector and a rotation of the second detector.

In yet another example embodiment herein, the movement apparatus comprises a carriage on which the first and second detectors are mounted such that the sensitive surfaces are substantially coplanar. In a further example embodiment herein, the movement apparatus changes between the first and second active configurations by means of a simultaneous translation of the carriage along a trajectory substantially perpendicular to the central axis of propagation.

According to one example embodiment herein, a radiological imaging device comprises a source that emits radiation that passes through at least part of a patient, the radiation defining a central axis of propagation. The device further comprises a receiving device, that includes at least one flat panel sensor that has a radiation sensitive surface for receiving the radiation and is arranged on the opposite side of the patient with respect to the source. The flat panel sensor is selectably operable in at least a flat panel mode and a linear sensor mode. In a further example embodiment herein, in the flat panel mode, the sensor performs at least one of fluoroscopy and tomography, and, in the linear sensor mode, performs at least one of radiography and tomography.

In some example embodiments herein, the radiological imaging device further comprises a gantry defining an analysis zone in which the at least part of the patient is placed; a bed suitable to support the patient and defining an axis of extension; a translation mechanism adapted to translate the source and the receiving device in a direction of movement substantially perpendicular to the central axis of propagation; a rotation mechanism adapted to rotate the source and the receiving device in relation to the axis of extension; at least one positioning laser mounted on the gantry that projects a positioning guidance marker onto the patient; a control unit adapted to configure, based on received information, at least one of an energy of the radiation and a radiation filter arranged to absorb at least a portion of the radiation before the radiation passes through the at least part of the patient; and a diaphragm suitable to shape the radiation into at least one of a cone beam or a fan beam.

Further features and advantages, as well as the structure and operation of various embodiments herein, are described in detail below with reference to the accompanying drawings.

BRIEF DESCRIPTION OF THE DRAWINGS

The characteristics of the example embodiments herein are clearly evident from the following detailed descriptions thereof, with reference to the accompanying drawings.

FIG. 1 illustrates a radiological imaging device according to an example embodiment herein.

FIG. 2a illustrates a cross-section of the radiological imaging device of FIG. 1.

FIG. 2b is a table showing predetermined relationships for configuring an X-ray source according to an example embodiment herein.

FIGS. 3a and 3b illustrate alternate configurations of a detector subassembly of the radiological imaging device of FIG. 1 according to an example embodiment herein.

FIGS. 4a and 4b illustrate alternate configurations of a detector subassembly of the radiological imaging device of FIG. 1 according to another example embodiment herein.

FIG. 9b illustrates a perspective view of the gantry subassembly shown in FIG. 9a.

DETAILED DESCRIPTION OF THE PREFERRED EMBODIMENTS

Figure 2C:
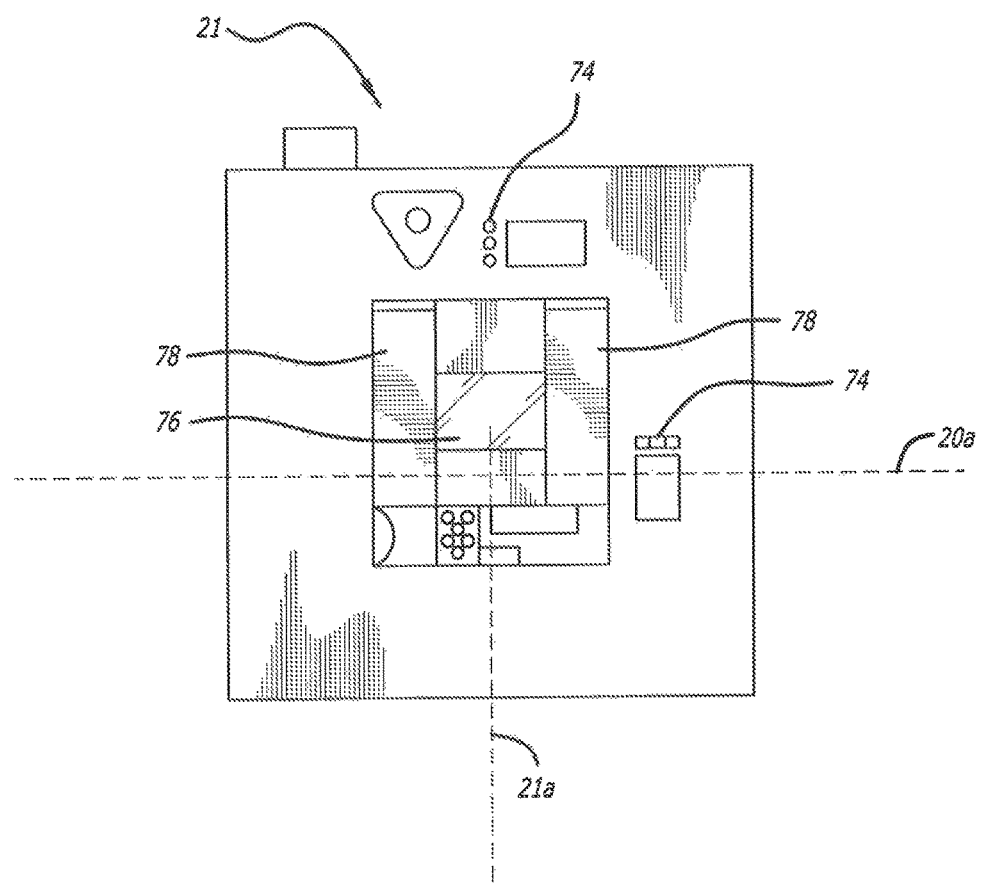
FIG. 2c depicts a source subassembly of the imaging device of FIG. 1 according to an example embodiment herein.

With reference to said drawings, reference numeral 1 globally denotes the radiological imaging device.

The device is useful in both the medical and veterinary spheres for performing radiological imaging of at least one portion of the internal anatomy of a patient. In particular, the radiological imaging device 1 is useful for performing two and three-dimensional scans and, more precisely, to selectively perform a radiography, a tomography (e.g., computerized tomography), or a fluoroscopy.

Figure 9A:
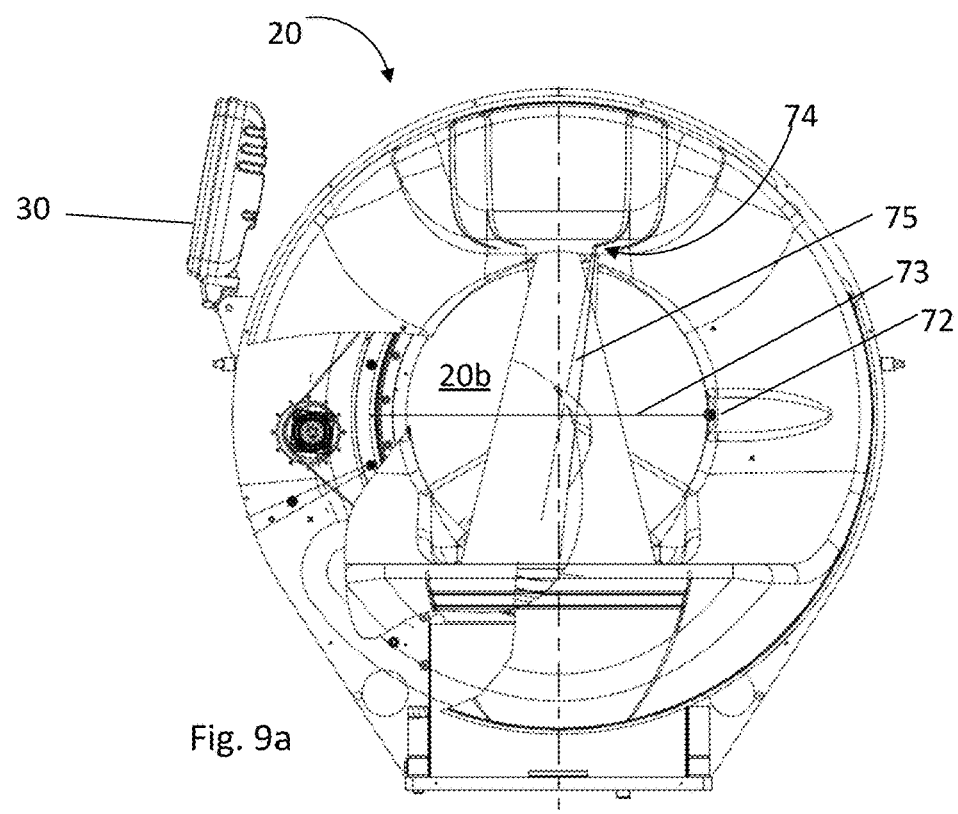
FIG. 9a illustrates a gantry subassembly, with a cut-away portion, according to an example embodiment of the radiological imaging device of FIG. 1.
Figure 9B:
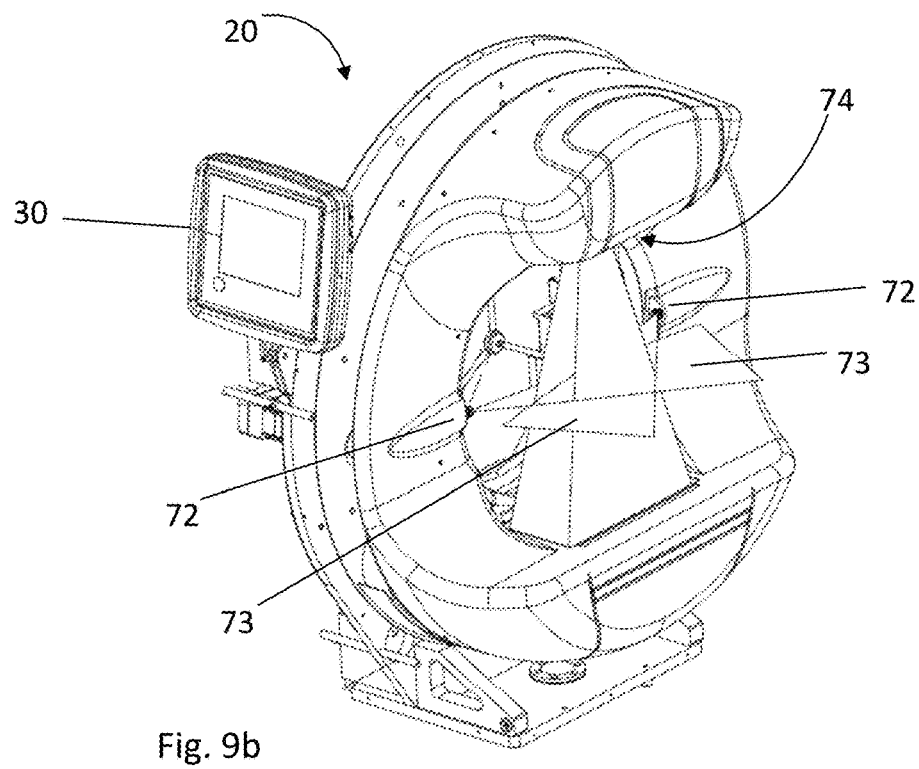

The radiological imaging device 1 comprises a gantry 20 defining a preferred axis of extension 20a and an analysis zone 20b in which at least part of the portion of the patient's body to be imaged is placed; and a control unit 30 appropriately placed in data transfer connection with the gantry 20 so as to control the operation thereof. In one example embodiment, the control unit 30 is mounted to the gantry 20 (as shown in FIGS. 1, 9a, and 9b), although in other examples it can be housed in a stand-alone unit (not shown) such as, for example, a workstation cart, or may formed of multiple parts, such as a first part mounted to the gantry 20 and a second part housed in a stand-alone unit (not shown). These examples are merely illustrative in nature, and in other embodiments, the control unit 30 can be located at other positions and locations besides those described above.

The gantry 20 constitutes a container within which the various components used to perform the radiological scan are housed (FIG. 2a). It thus comprises a source 21 to emit radiation defining a central axis of propagation 21a; a receiving apparatus 22 to receive the radiation emitted by the source 21; and a casing 23 at least partially containing the source 21 and the receiving apparatus 22. Additionally, in a further example embodiment herein, the gantry 20 further comprises a laser positioning system that includes at least one horizontal laser 72 and at least one vertical laser 74 (FIGS. 9a and 9b). The foregoing subcomponents of the gantry 20 will now be described in turn.

The source 21 is suitable to emit, in a known manner, radiation capable of traversing the body of the patient, and interacting with the tissues and fluids present inside the patient. In one example embodiment herein, the source 21 emits as ionizing radiation, and more particularly, X-rays.

In relation to the source, the device 1 comprises a collimator to focus the radiation on the receiving device 22 and to vary the focus zone in order to adjust it to the position of the receiving device 22, as described more fully below.

FIG. 2c depicts the source 21 of the radiological imaging device 1 of FIG. 1, according to an example embodiment herein. As represented in FIG. 2a and shown in FIG. 2c, in one example embodiment herein, an X-ray filter 76 can optionally be positioned in front of the source 21 and function to modify the energy distribution of the radiation emitted by the source 21 along the axis of propagation 21*a* (e.g., by absorbing low power X-rays) prior to the X-rays traversing the patient (although source 21 also may be operated without an X-ray filter 76). The X-ray filter 76 may comprise an aluminum and/or copper sheet (or any other material suitable for the absorption of radiation) of predetermined thickness.

In another example embodiment herein, a plurality of X-ray filters (not shown) are stored at different locations in the gantry 20, each of the plurality of X-ray filters differing from others of the filters in terms of at least one of a type of material (such as an aluminum and/or copper sheet) or thickness. The control unit 30 can cause a motorized mechanism (not shown) provided within the gantry 20 to retrieve a selected X-ray filter (e.g., selected by control unit 30 in a manner to be described further herein below) from storage and position the selected X-ray filter in front of the source 21.

In a further example embodiment herein, the operator can operate control unit 30 to input information, such as, for example and without limitation, a type of the imaging procedure selected to be performed (e.g., fluoroscopy, tomography, or radiography), a type of patient species, the patient's weight, and/or tissue type to be imaged, and cause the control unit 30 to automatically configure the radiological imaging device 1 to use an optimal radiation dosage. In response, the control unit 30 determines an X-ray emission energy from the source 21 (X-ray emission energy being a function of parameters including X-ray tube voltage, X-ray tube current, and exposure time) and/or a type of X-ray filter 76 to employ, so that the radiological imaging device 1 can perform the selected imaging procedure with an X-ray dosage that is safe for the patient, as well as the operator, while maintaining optimal image quality.

For example, the control unit 30 can perform the aforementioned determination of X-ray emission energy and/or select an X-ray filter type based on predetermined relationships (e.g., defined in accordance with look-up table(s), conditional statement algorithm(s), and/or mathematical formula(s) implemented on control unit 30, although these examples are not limiting) between the patient information, the radiological imaging procedure selected to be performed, the X-ray emission energy, and the materials and thicknesses of the X-ray filters available in the plurality of X-ray filters located inside the gantry. Examples of such predetermined relationships are shown in the table of FIG. 2*b*.

As but one non-limiting example, if an operator specifies as input (by way of control unit 30) that high resolution tomography is to be performed on hard tissues (e.g., a thorax region), the control unit 30 determines, via a look up table, for example, that the aforementioned input correlates to operating parameters for the source 21 of 100 kV and 60 mA for 5 ms and an X-ray filter 76 of a type comprising a 3 mm thick sheet of aluminum together with a 0.2 mm thick sheet of copper (see FIG. 2*b*). As another example, if an operator specifies (by way of the control unit 30) that high resolution tomography is to be performed on soft tissues (e.g., an abdominal region), the control unit 30 determines, via a look-up table, for example, that that input correlates to operating parameters for the source 21 of 60 kV and 60 mA for 10 ms and an X-ray filter 76 of a type comprising a 2 mm thick sheet of aluminum (see FIG. 2*b*).

In yet another example embodiment herein, the source 21 is selectably configured (e.g., by control unit 30) to emit either a cone-shaped beam of radiation or a fan-shaped beam of radiation, by configuring the shape of an adjustable diaphragm 78. The adjustable diaphragm 78, shown in FIG. 2*c*, comprises at least two movable plates 78*a* and 78*b* capable of substantially blocking radiation, the plates 78*a* and 78*b* being movable into at least one of an open configuration or a slit configuration by a motorized mechanism (not shown) under operator control by way of control unit 30. When the adjustable diaphragm 78 is configured in the open configuration, radiation from the source 21 is not blocked and emits along the axis of propagation 21*a* in the shape of a cone. When the adjustable diaphragm 78 is configured as a slit, a portion of the radiation of the source 21 is blocked, and thus radiation emits along the axis of propagation 21*a* in the shape of a fan (i.e., a cross-section of the cone-shaped radiation) oriented perpendicularly to the direction of extension 20*a*. Thus, in one example embodiment herein, an operator may configure the source 21 to emit either a cone-shaped beam or a fan-shaped beam by virtue of the adjustable diaphragm 78, and perform different types of imaging with the radiological imaging device 1, such as, for example, cone beam tomography or fan beam tomography, respectively.

The laser positioning system (including horizontal laser(s) 72 and vertical laser(s) 74 mounted in the gantry 20), when activated on the control unit 30, projects visual markers onto the patient in order to facilitate positioning of the patient on the bed 40, and more particularly, within the analysis zone 20*b*. In particular, in one example embodiment herein, the laser positioning system is used in conjunction with an adjustable bed (serving as bed 40), according to one or more of the example embodiments described in U.S. Provisional Patent Application Nos. 61/932,034 and 61/944,956, which are incorporated herein by reference in their entireties, as if set forth fully herein. Referring to FIGS. 9*a* and 9*b*, which illustrate a gantry 30 according to an example embodiment of the radiological imaging device illustrated in FIG. 1, the laser positioning system includes at least one horizontal laser 72, which projects horizontal visual markers 73 to aid the operator in adjusting the height and inclination of the patient, and/or at least one vertical laser 74, which projects a top-down marker 75 to aid the operator in adjusting the lateral centering of the patient with respect to the gantry 20. The operator adjusts the positioning of the patient by observing the position of the patient with respect to the projected laser markers 73 and 75, and thus with respect to the analysis zone 20*b*, and then, for example, manually repositioning the patient on the bed 40 or by adjusting controls on the aforementioned adjustable bed (not shown in FIGS. 9*a* and 9*b*) until the patient is deemed by the operator to be in the correct position for imaging.

The receiving device 22 is arranged on the opposite side of the analysis zone 20*b* and, in particular, of the patient, with respect to the source 21, so as to detect radiation after it has traversed the portion of the patient's body to be examined. In response to detecting radiation, receiving device 22 outputs corresponding data signals to the control unit 30 at a particular frame rate, and the control unit 30, in turn, processes the data signals to acquire images.

The receiving device 22 can be operated in a selected one of a first active configuration suitable for performing tomography and fluoroscopy or a second active configuration suitable to perform at least radiography, as will now be described. By virtue of the receiving device 22 being operable in either a first active configuration or a second active configuration, an operator can perform tomography, fluoroscopy, and radiography in the same radiological imaging device 1. Various example embodiments of the receiving device 22 are illustrated in FIGS. 3a-7b. The example embodiments of the receiving device 22 will now be discussed in turn.

In one example embodiment of the receiving device 22 herein, the receiving device 22 comprises at least a first detector 24 to selectively perform tomography or fluoroscopy and defining a first sensitive surface 24a to detect the radiation; at least a second detector 25 to perform radiography and defining a second sensitive surface 25a to detect the radiation; and a movement apparatus 26 to move the first detector 24 and the second detector 25 with respect to the source 21 so as to configure the receiving device 22 into the first or second active configurations.

In further example embodiments herein, the first detector 24 comprises a flat panel sensor 24b (FIGS. 3a-6b), while the second detector 25 comprises at least one linear sensor (e.g., linear sensor 25b illustrated in FIG. 6b), in particular, two linear sensors 25b and 25c arranged side by side and, more in particular, two linear sensors 25b and 25c together defining a second sensitive surface 25a that are substantially coplanar (e.g., FIGS. 3a-5b). The linear sensor(s) 25b and 25c can have a frame rate in the range of approximately 50 frames per second to approximately 300 frames per second, in one example.

In some cases, the receiving device 22 may be provided with a third detector, not illustrated in the drawings, which, in one example embodiment herein, comprises a direct photonic counting sensor.

The movement apparatus 26 is suitable to move the detectors 24 and 25 with respect to the source 21 into the first active configuration (FIGS. 3a, 4a, 5a and 6a) in which only the first detector 24 is able to receive the radiation emitted by the source 21 and into the second active configuration (FIGS. 3b, 4b, 5b and 6b) in which only the second detector 25 is able to receive said radiation.

In detail, the movement apparatus 26 moves the detectors 24 and 25 in such a way that, in their respective active configurations, the sensitive surfaces 24a and 25a are substantially perpendicular to the central axis 21a and the distances from the detectors 24 and 25 (more precisely, the surfaces 24a and 25a) to the source 21 are substantially the same. The operation of the movement apparatus 26 with respect to the example embodiments illustrated in FIGS. 3a-6b will be described further herein below.

Furthermore, in the case in which the receiving device 22 envisages said third detector, the movement apparatus 26 moves the three detectors, in the same way as described below, to define a third active configuration in which the third detector is the only one able to receive the radiation emitted by the source 21; in which the sensitive surface of said third detector is substantially perpendicular to the central axis of propagation 21a; and in which the distance of the source 21 from the third detector and, more precisely, from its sensitive surface, is equal to that defined by said source 21 and by the other surfaces 24a and 25a in their respective active configurations.

FIGS. 3a and 3b illustrate one example embodiment of the receiving device 22 in which a flat panel sensor 24b is employed as a first detector 24 and two linear sensors 25b and 25c are employed as a second detector 25. As shown in FIGS. 3a and 3b, the movement apparatus 26 comprises a load-bearing body 26a to support the detectors 24 and 25 and a motor 26b, such as an electric motor, to rotate the detectors 24 and 25 along an axis of rotation 26c. The rotation may be substantially perpendicular to the central axis of propagation 21a and, more particularly, substantially parallel to or perpendicular to the preferred axis 20a.

In a further example embodiment herein, the amplitude of rotation of the detectors 24 and 25 is substantially equal to 90° or 180° so that, in the first active configuration (FIG. 3a), the first surface 24a is substantially perpendicular to the central axis of propagation 21a and the second surface 24a is substantially parallel to the axis 21a; whereas, in the second active configuration (FIG. 3b), the first surface 24a is substantially parallel to the central axis of propagation 21a and the second 26a is substantially perpendicular to the axis 21a.

Furthermore, as shown in FIGS. 3a and 3b, the movement apparatus 26 may be provided with an additional linear actuator 26d to move the first detector 24 along a direction of analysis substantially perpendicular to the central axis 21a and, in particular, substantially perpendicular to the direction 20a and, more particularly, substantially parallel to the axis 26c.

FIGS. 4a and 4b illustrate a variation of the example embodiment of the receiving device 22 in which a flat panel sensor 24b is employed as a first detector 24 and two linear sensors 25b and 25c are employed as a second detector 25. As shown in FIGS. 4a and 4b, the apparatus 26 is useful for changing the active configuration by mutually translating the detectors 24 and 25.

In that case, the movement apparatus 26 comprises a first linear actuator 26e to move the first detector 24 along a first direction of translation 26f and a second linear actuator 26g to move the second detector 25 along a second direction of translation 26h. In an example embodiment herein, the directions of translation 26f and 26h are substantially perpendicular to the direction 20a. In another example embodiment herein, the first direction 26f is substantially perpendicular to the central axis of propagation 21a and the second direction 26h is substantially parallel to the central axis of propagation 21a.

As an alternative to the second actuator 26g, the movement apparatus 26 may be provided with a lever mechanism or other kinematic mechanism, which, appropriately activated by the first linear actuator 26e, moves the second detector 25 along the second direction 26h.

Figure 5A:
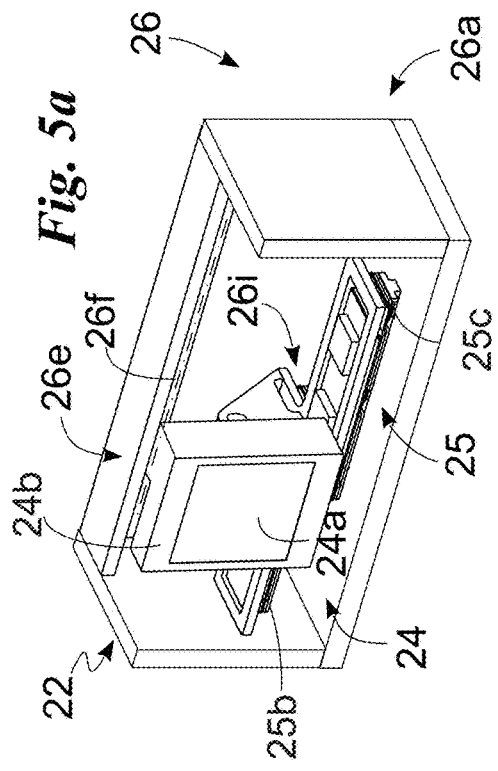
FIGS. 5a and 5b illustrate alternate configurations of a detector subassembly of the radiological imaging device of FIG. 1 according to another example embodiment herein.
Figure 5B:
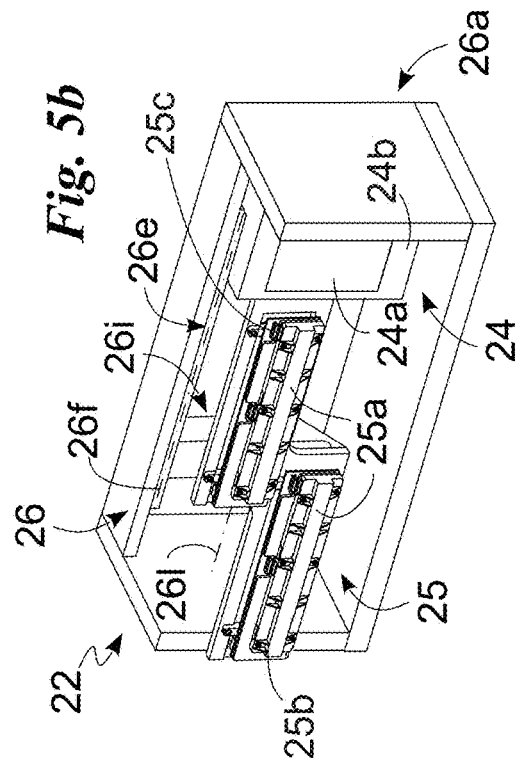

FIGS. 5a and 5b illustrate another variation of the example embodiment of the receiving device 22 in which example a flat panel sensor 24b is employed as a first detector 24 and two linear sensors 25b and 25c are employed as a second detector 25. As shown in FIGS. 5a and 5b, the apparatus 26 is provided with an additional rotational actuator 26i to rotate, for example by 90° or by 180°, the second detector 25 so that, when the first linear actuator 26e has moved the first detector 24 away, said second detector 25 substantially occupies the space left free by the translation along the first direction 26f of the first sensor 24. In particular, the additional rotational actuator 26i may rotate the second detector 25 with respect to an additional axis of rotation 26l, such as parallel to the first direction of translation 26f.

In this case, in the first active configuration (FIG. 5a), the first detector 24 substantially overlaps the second detector 25 so that only the first detector 24 receives the radiation. In the second active configuration (FIG. 5b), the detectors 24 and 25 are arranged side by side and placed so that the second sensitive surface 25a is the only one to be hit by the radiation and is substantially coplanar with the first sensitive surface 24a.

Additionally, the first actuator 26e may move the first detector 24 to one or more intermediate positions between those assumed by said first detector 24 in said first and second active configurations.

Figure 6A:
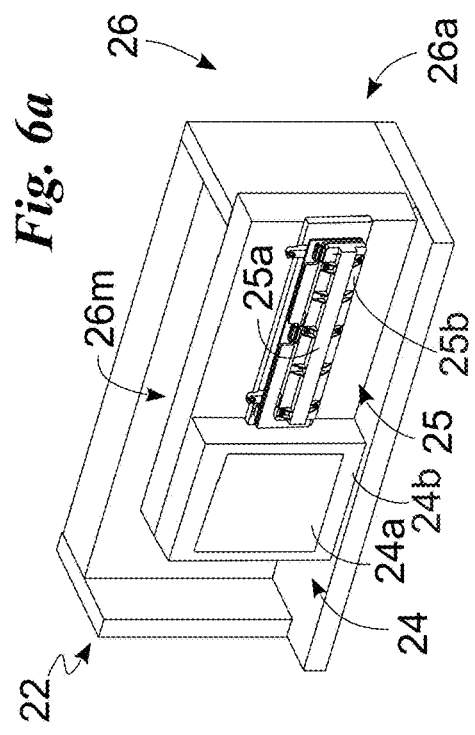
FIGS. 6a and 6b illustrate alternate configurations of a detector subassembly of the radiological imaging device of FIG. 1 according to another example embodiment herein.
Figure 6B:
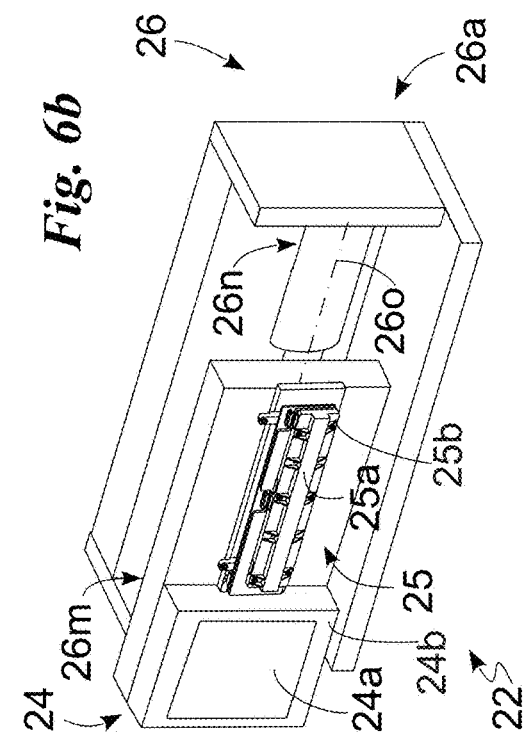

FIGS. 6a and 6b illustrate still another example embodiment of the receiving device 22 in which example a flat panel sensor 24b is employed as a first detector 24 and at least one linear sensor 25b is employed as a second detector 25. As shown in FIGS. 6a and 6b, the movement apparatus 26 comprises a carriage 26m on which both of the detectors 24 and 25 are mounted such that the sensitive surfaces 24a and 25a are substantially coplanar and, in a further example embodiment herein, substantially perpendicular to the central axis 21a.

In this example embodiment, the movement apparatus 26, in order to modify the active configuration of the receiving device 22, provides, in addition to the carriage 26m, a linear mover 26n (for example a linear actuator) to move the carriage 26m and, therefore, simultaneously move the detectors 24 and 25 along an additional trajectory 26o that is substantially perpendicular to the central axis of propagation 21a. In another example embodiment herein, the trajectory 26o is substantially perpendicular to the central axis of propagation 21a and the preferred axis of extension 20a so as to keep the sensitive surfaces 24a and 25a always for substantially perpendicular to the central axis 21a.

In detail, the linear mover 26n is adapted to move the carriage 26m defining a plurality of second active configurations allowing the detectors 24 and 25 to perform a series of radiological imaging about adjacent portions and, therefore, allowing the device 1 to execute imaging of portions that are larger than the sensitive surfaces 24a and 25a.

Figure 7A:
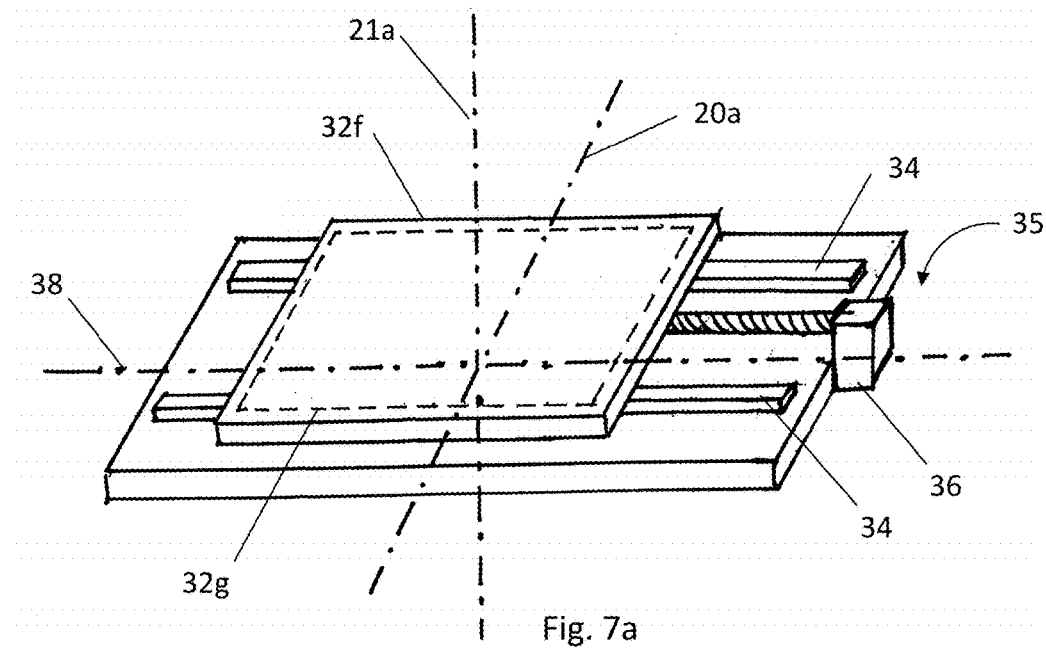
FIG. 7a illustrates a matrix mode of a flat panel sensor subassembly of the imaging device of FIG. 1 according to an example embodiment herein.
Figure 7B:
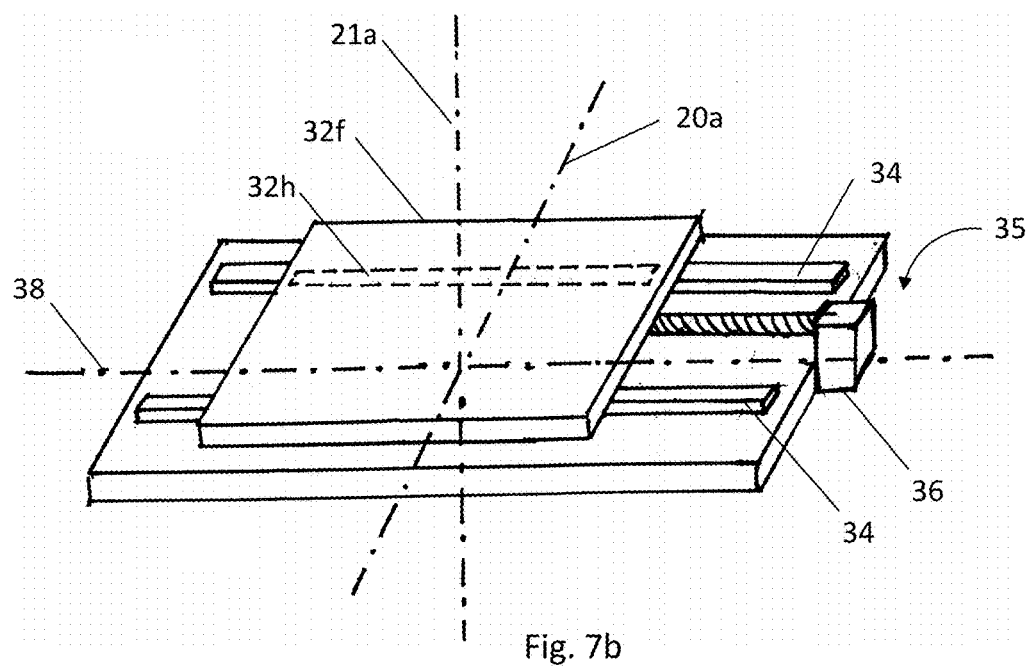
FIG. 7b illustrates a linear sensor mode of a flat panel sensor subassembly of the imaging device of FIG. 1 according to an example embodiment herein.

Another example embodiment of the detector 22 will now be described. In this embodiment, the detector 22 comprises at least one flat panel sensor 32f (as shown in FIGS. 7a and 7b), that includes an array of pixels and is capable of operating in multiple independent read-out modes, selectable by control unit 30, including at least a matrix mode (FIG. 7a) and a linear sensor mode (FIG. 7b). In this example embodiment of the receiving device 22, operating the flat panel sensor 32f in the matrix mode is referred to as the first active configuration of the receiving device 22, and operating the flat panel sensor 32f in the linear sensor mode is referred to as the second active configuration of the receiving device 22.

In the first active configuration (the matrix mode), the flat panel sensor 32f outputs, to control unit 30, signals corresponding to radiation detected by pixels in a region of sensitive surface 32g (FIG. 7a). In one example embodiment herein, the sensitive surface 32g is substantially coextensive with the entire array of pixels of the flat panel sensor 32f. The flat panel sensor mode is suitable for performing at least tomography and fluoroscopy.

In the second active configuration (linear sensor mode), the flat panel sensor 32f outputs, to control unit 30, signals corresponding to radiation detected by the subset of pixels in a region of sensitive surface 32h (FIG. 7b). The sensitive surface 32h functions effectively as a linear sensor (e.g., in a manner similar to linear sensors 25b and 25c); that is, in one example, the sensitive surface 32h has a frame rate in the range of approximately 50 frames per second to approximately 300 frames per second and has a width that is substantially greater than its length, its length being defined in a direction substantially parallel to direction 20a and its width being defined substantially perpendicular to the direction of movement 20a and the central axis of propagation 21a.

In one example embodiment herein, the second active configuration of the flat panel sensor 32f is useful for performing fan beam tomography. As described above (with reference to FIG. 2c), fan beam tomography can be performed by shaping the radiation emitted by the source 21 into a fan-shaped beam using, for example, diaphragm 78. However, by virtue of the ability of flat panel sensor 32f to operate a selected one of multiple modes (selectable by control unit 30), it is possible to switch from fan beam imaging to cone beam imaging without physically interchanging any components of the radiological imaging device 1 and without altering the operation of source 21, by selecting (via control unit 30, for example) a portion (i.e., a subset) of the flat panel sensor 32f as a radiation sensitive surface. That is, for a cone-shaped beam of radiation, operating the flat panel sensor 32f in the linear sensor mode will provide the sensitive surface 32h that is effectively sensitive only to a fan-shaped cross-section of the cone-shaped beam of radiation. Accordingly, when the source 21 emits a cone-shaped beam of radiation, cone beam tomography can be performed by selecting via control unit 30, for example, the matrix mode of flat panel sensor 32f, and fan beam tomography can be performed by selecting via control unit 30, for example, the linear sensor mode of flat panel sensor 32f.

The pixel array size of sensitive surfaces 32g and 32h can be predefined for the flat panel sensor 32f in hardware, firmware, software, or other means by which the flat panel sensor 32f may be controlled.

In particular, in one example embodiment herein, the flat panel sensor 32f may be a Hamamatsu model C11701DK-40 flat panel sensor, which can operate in a matrix mode that provides a sensitive surface 32g, having a 1096×888 array of pixels or a 2192×1776 array of pixels, and can also separately operate in a linear sensor mode that provides a sensitive surface 32h, having a 1816×60 array of pixels.

Additionally, the flat panel sensor 32f can be mounted on a panel motion system 35 that includes guides 34 and a motorized translation mechanism 36 (FIGS. 7a and 7b). The panel motion system 35 is suitable for moving the flat panel sensor 32f along an axis 38, which is substantially perpendicular to both the gantry direction of movement 20a and the central axis of propagation 21a. In particular, the axis 38 is also parallel to the width of the sensitive surface 32h when the flat panel sensor 32f is operating in the linear sensor mode.

In addition to the foregoing components, the gantry 20 is provided with a rotation mechanism 27 to rotate the source 21 and the receiving device 22 together, the rotation being substantially around the preferred axis of extension 20a so as to allow the radiological imaging device 1 to perform scanning around 360° of the portion of the patient that has been placed in the analysis zone 20b (FIG. 2a).

In one example embodiment herein, the rotation mechanism 27 comprises a rotor 27a, such as a permanent magnet rotor, to which the source 21 and the receiving device 22 are connected, and a stator 27b, integrally connected to the casing 24, to emit a magnetic field controlling the rotation of the rotor 27a about the preferred axis of extension 20a. Operation of the rotation mechanism 27 can be controlled by the control unit 30.

The imaging device 1 may comprise a bed 40 to support the patient partially inserted in the analysis zone 20b and a load-bearing structure 50 to hold the gantry 20 and the bed 40 in the correct position (FIG. 1). In particular, the load-bearing structure 50 comprises a base 51; at least one column 52, more particularly two columns, to support the bed 40; and a translation mechanism 53. The translation mechanism 53 comprises a linear guide 54, positioned between the gantry 20 and the load-bearing structure 50, and a carriage 55, suitable to slide along the linear guide 54. In an example embodiment herein, the linear guide 54 may be a motorized linear guide or, more specifically, an electric motorized linear guide. Accordingly, the translation mechanism 53 is suitable to move the gantry 20 with respect to the base 51 along the preferred axis of extension 20a, so as to permit the radiological imaging device 1 to perform radiological imaging over practically the entire length of the bed 40. Additionally, the translation of the gantry 20 by the translation mechanism 50 can be controlled by the control unit 30.

Figure 10:
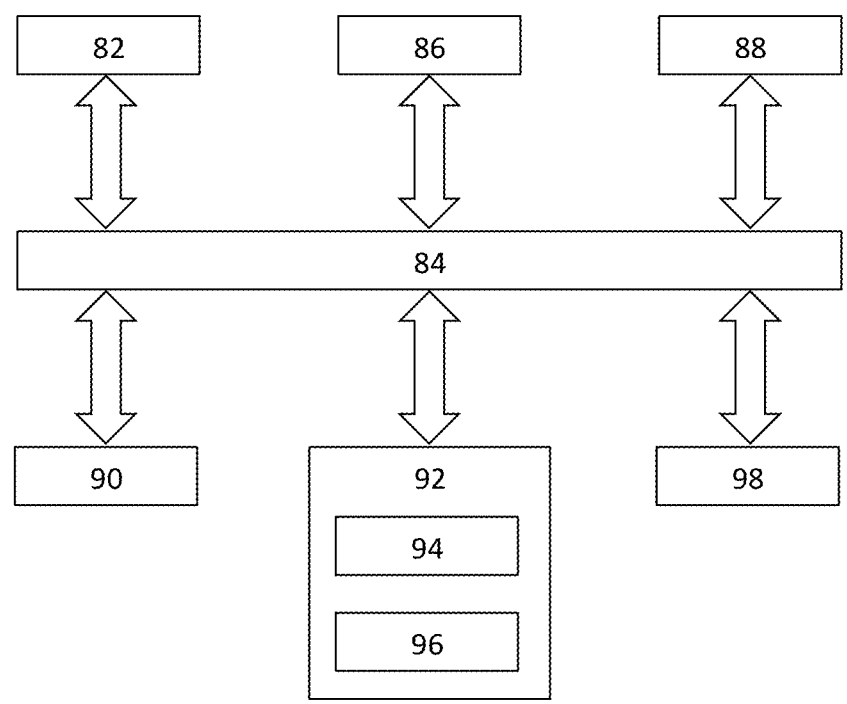
FIG. 10 illustrates a block diagram of an example computer system of the radiological imaging system shown in FIG. 1.

FIG. 10 illustrates a block diagram of a computer system 80. In one example embodiment herein, at least some components of the computer system 80 can form or be included in the aforementioned control unit 30, and computer system 80 is electrically connected to other components of the radiological imaging device 1 (such as, for example, the source 21, the receiving device 22, the gantry 20, and any subcomponents thereof) by way of communications interface 98 (mentioned below). The computer system 80 includes at least one computer processor 82 (also referred to as a "controller"). The computer processor 82 may include, for example, a central processing unit, a multiple processing unit, an application-specific integrated circuit ("ASIC"), a field programmable gate array ("FPGA"), or the like. The processor 82 is connected to a communication infrastructure 84 (e.g., a communications bus, a cross-over bar device, or a network). Although various embodiments are described herein in terms of this exemplary computer system 80, after reading this description, it will become apparent to a person skilled in the relevant art(s) how to implement the invention using other computer systems and/or architectures.

The computer system 80 may also include a display unit 86 for displaying video graphics, text, and other data provided from the communication infrastructure 84. In one example embodiment herein, the display unit 86 can form or be included in the control unit 30.

The computer system 80 also includes an input unit 88 that can be used by the operator to send information to the computer processor 82. For example, the input unit 88 can include a keyboard device and/or a mouse device or other input device(s). In one example, the display unit 86, the input unit 88, and the computer processor 82 can collectively form a user interface.

In an example embodiment that includes a touch screen, for example, the input unit 88 and the display unit 86 can be combined. In such an embodiment, an operator touching the display unit 86 can cause corresponding signals to be sent from the display unit 86 to a processor such as processor 82, for example.

In addition, the computer system 80 includes a main memory 90, which preferably is a random access memory ("RAM"), and also may include a secondary memory 92. The secondary memory 92 can include, for example, a hard disk drive 94 and/or a removable storage drive 96 (e.g., a floppy disk drive, a magnetic tape drive, an optical disk drive, a flash memory drive, and the like) capable of reading from and writing to a corresponding removable storage medium, in a known manner. The removable storage medium can be a non-transitory computer-readable storage medium storing computer-executable software instructions and/or data.

The computer system 80 also can include a communications interface 98 (such as, for example, a modem, a network interface (e.g., an Ethernet card), a communications port (e.g., a Universal Serial Bus ("USB") port or a FireWire® port), and the like) that enables software and data to be transferred between the computer system 80 and external devices. For example, the communications interface 98 may be used to transfer software or data between the computer system 80 and a remote server or cloud-based storage (not shown). Additionally, the communication interface 98 may be used to transfer data and commands between the computer system 80 (serving as control unit 30) to other components of the radiological imaging device 1 (such as, for example, the source 21, the receiving device 22, the gantry 20, and any subcomponents thereof).

One or more computer programs (also referred to as computer control logic) are stored in the main memory 90 and/or the secondary memory 92 (i.e., the removable-storage drive 96 and/or the hard disk drive 94). The computer programs also can be loaded into the computer system 80 via the communications interface 98. The computer programs include computer-executable instructions which, when executed by the controller/computer processor 82, cause the computer system 80 to perform the procedures described herein and shown in at least FIG. 8, for example. Accordingly, the computer programs can control the control unit 30 and other components (e.g., the source 21, the receiving device 22, the gantry 20, and any subcomponents thereof) of the radiological imaging device 1.

Example embodiments of a method for using a radiological imaging device 1 (described above in a structural sense) will now be further described. Generally, example embodiments of the method include a novel and innovative radiological imaging procedure primarily comprising a positioning phase in which the operator arranges the patient on the bed 40; at least one preparatory phase in which the operator prepares the patient for the radiological imaging procedure; at least one control phase in which a check is performed to verify the correct condition of the patient; and an analysis phase in which at least one radiological imaging procedure is performed.

In particular, the preparatory phase and the control phase, and in another example embodiment herein, also the analysis phase, are performed while keeping the patient substantially still (i.e., without moving the patient) with respect to the radiological imaging device 1, more precisely, keeping the patient substantially still with respect to the gantry 20 and, yet more precisely, keeping the patient on the bed 40 and partially placed in the analysis zone 20b. More in particular, said phases are performed, as described below, so as to involve, at the very most, small movements of the patient without altering the position thereof with respect to the device and, in particular, to the gantry 20.

Figure 8:
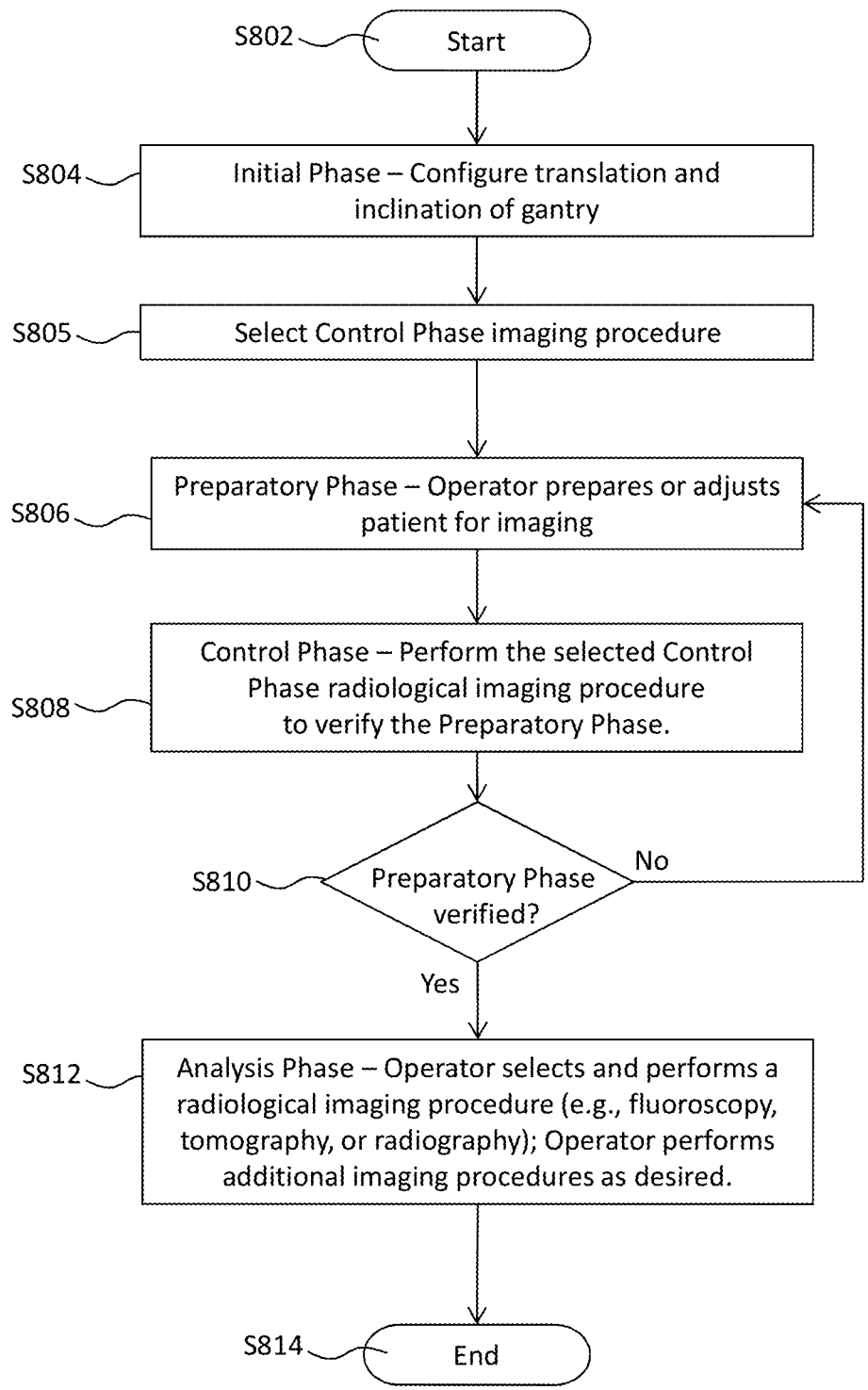
FIG. 8 is a flowchart illustrating an imaging procedure according to an example embodiment herein.

An example embodiment of the foregoing method of using the radiological imaging device 1 will now be described further in detail, with reference to FIG. 8. The process starts in Step S802.

In an initial phase at Step S804, after laying the patient on the bed 40, the operator uses the control unit 30 to place the gantry 20 in a working configuration and to translate the gantry 20 along the axis 20a to the zone to be examined. The operator also uses the control unit 30 to select the inclination of the central axis of propagation 21a with respect to the bed.

In one example embodiment herein, the operator activates the laser positioning system during Step S804 (comprising lasers 72 and 74, as shown in FIGS. 9a and 9b), which projects horizontal visual markers 73 to assist the operator in adjusting the height and inclination of the patient with respect to the gantry 20, and/or projects a top-down marker 75 to assist the operator in laterally adjusting the patient with respect to the gantry 20.

Additionally in Step S804, the operator also may operate the control unit 30 to input patient information (e.g., species, weight, and/or tissue type to be imaged), and may further command the control unit 30 to automatically configure the radiological imaging device 1 to select an appropriate radiation dose based on the patient information and the imaging procedure to be performed, in the above described manner. Accordingly, in some of the steps that follow (in particular, Steps S808 and S812), the control unit 30 may configure, in the manner described above, the X-ray source 21 and the X-ray filter 76 so as to be prepared to provide an appropriate radiation dose based on the patient information and the imaging procedure to be performed in that step.

In Step S805, the operator selects (e.g., via control unit 30) the test radiological imaging procedure to be performed in the subsequent control phase, such as tomography, fluoroscopy, or radiography (preferably fluoroscopy). In response to the selection of the test radiological imaging procedure, the receiving device 22 is configured by control unit 30 into the first or second active configuration accordingly, in the manner described above.

In particular, in response to a fluoroscopy procedure being selected, and in embodiments in which the receiving device 22 includes a first detector 24, a second detector 25, and a movement apparatus 26 (illustrated in FIGS. 3a-6b), the control unit 30 sends a command to the movement apparatus 26 to move the sensors 24 and 25 with respect to the source 21 so as arrange them in the first active configuration, that is to say, so that only the first sensitive surface 24a can be hit by the radiation emitted by the source 21.

In the example embodiment in which the receiving device 22 employs a flat panel sensor 32f capable of selectably operating in one of a matrix mode and a linear sensor mode (FIGS. 7a and 7b), Step S805 is performed by the control unit 30 responding to the operator selecting the fluoroscopy procedure by controlling the flat panel sensor 32f to operate it in the first active configuration (the matrix mode), that is, the flat panel sensor 32f utilizes a two-dimensional sensitive surface 32g to detect radiation emitted by the source 21.

Next, in a preparatory phase at Step S806, the operator, with the patient on the bed 40, prepares the patient for the radiological imaging procedure by injecting a contrast liquid and/or placing the portion to be examined in the correct position and/or at the correct angle (e.g., superimposing the shoulder joint on the trachea).

Practically simultaneously (although not necessarily), the control phase commences at Step S808 in which the operator, using the radiological imaging device 1, generates images by running the test radiological imaging procedure selected in Step S805, such as fluoroscopy (in one example), and visually verifies the correct condition of the patient by way of those images, that is to say, to verify that the preparatory phase of Step S806 was performed correctly.

In particular, in the case where a contrast liquid was injected in Step S806, in Step S808, the operator monitors the progress of the contrast liquid by way of images acquired by the test radiological imaging procedure, i.e., fluoroscopy in particular, to determine (in block S810) whether or not the contrast liquid has reached the analysis zone and, thus, whether the next imaging procedure should be performed. In particular, if the contrast liquid has not yet reached the analysis zone ("No" in block S810), the operator continues to monitor (in Step S808) the progress of the contrast liquid until it reaches the desired zone, thus indicating (i.e. "Yes" in block S810) that the preparatory phase was performed correctly and that the procedure may proceed to the analysis phase at Step S812.

Alternatively, if the portion to be examined needs to be in a certain position or at a given angle, in Step S808, the operator checks whether that portion of the patient is positioned correctly based on images generated by the test radiological imaging procedure (i.e., fluoroscopy or radiography). In detail, if it is determined at block S810 that the portion of the patient to be imaged is not in the desired position, the operator may perform the preparatory phase at Step S806 again to adjust the position or angle of the patient and, substantially simultaneously, the operator may perform a new control phase at Step S808 to verify, instant by instant, whether the new position in which the patient has just been placed is the desired position.

When it has been verified at block S810 (based on the test radiological imaging performed in the control phase at Step S808) that the conditions are optimal or most suitable for the next phase to start ("Yes" at block S810), the analysis phase starts at Step S812.

In Step S812, the operator uses the control unit 30 to select an imaging procedure to be performed in the analysis phase, and in response, the control unit 30 places the radiological imaging device 1, and in particular, the receiving device 22, in the desired configuration (e.g., the first active configuration if tomography or fluoroscopy are selected or the second active configuration if radiography is selected). Thereafter, the operator performs the desired analysis phase imaging procedure.

For example, in the analysis phase, the operator may wish to perform tomography (also referred to as computed tomography) in order to produce three-dimensional rendered volumes or two-dimensional tomographic slices of a portion of the patient. In another instance, the operator may wish to perform fluoroscopy in order to acquire real-time moving images of a portion of the patient (such moving images can also be captured, in main memory 90 and/or secondary memory 92 for example, for replaying at a later time), the real-time moving images being useful for guiding interventional radiographic procedures, such as the placement of stents, although this example is not limiting. In yet another instance, the operator may wish to perform radiography to acquire a high-resolution image of at least a portion of the patient.

As but one non-limiting example, in response to the user selecting tomography or fluoroscopy, the control unit 30 configures the receiving device 22 into the first active configuration. That is, in the embodiment where the receiving device 22 includes a first detector 24, a second detector 25, and a movement apparatus 26 (e.g., FIGS. 3a-6b), the control unit 30 responds to the user specifying radiography by sending a command to the movement apparatus 26 to place the radiological imaging device 1 in the first active configuration (FIG. 3a, 4a, 5a, or 6a) by rotating the detectors 24 and 25 or, alternatively, through a mutual translational movement thereof. In the example embodiment in which the receiving device 22 employs a flat panel sensor 32f, the control unit 30 responds to a selection of tomography or fluoroscopy by controlling the flat panel sensor 32f to operate in the first active configuration, that is, in the matrix mode with sensitive surface 32g (FIG. 7b). If the operator selected tomography, the operator then operates the control unit 30 to perform the tomography procedure to acquire tomographic data, such as, for example, two-dimensional tomographic slices or a reconstructed three-dimensional volume. If the operator selected fluoroscopy, the operator operates the control unit 30 to perform fluoroscopy to acquire a real-time moving x-ray image of a portion of the patient.

In particular, in the example embodiment in which a flat panel sensor 24b is employed as the first detector 24 and two linear sensors 25b and 25c are employed as the second detector 25 (e.g., FIGS. 3a-5b), the portion of the patient to be analyzed is larger than the first surface 24a, the first detector 24 is moved, for example by the first actuator 26e (or, alternatively, by the additional linear actuator 26d) along the first direction 26f and the collimator focuses the radiation on the new position of the first detector 24 in order to permit the analysis (i.e., acquire an image) of a new portion adjacent to the previous portion. Similarly, in the example embodiment in which the receiving device 22 employs the flat panel sensor 32f (FIGS. 7a and 7b), and the surface to be analyzed is larger than the sensitive surfaces 32g or 32h, the flat panel sensor 32f can be translated to one or more adjacent positions by the panel motion system 35 along axis 38 in order to permit further analysis (i.e., acquiring additional images) until the entire body portion to be analyzed has been imaged.

By way of example only, the operator may wish to select radiography to be performed in the analysis phase, in Step S812. Accordingly, the operator specifies radiography using the control unit 30, and in response, the control unit 30 configures the receiving device 22 into the second active configuration. In particular, in the embodiment where the receiving device 22 includes a first detector 24, a second detector 25, and a movement apparatus 26 according to any of the example embodiments illustrated in FIGS. 3a-6b, the control unit 30 responds to the user specifying radiography by sending a command to the movement apparatus 26 to place the radiological imaging device 1 in the second active configuration (FIG. 3b, 4b, 5b, or 6b) by rotating the detectors 24 and 25 or, alternatively, through a mutual translational movement thereof. In the example embodiment of the receiving device 22 employing a flat panel sensor 32f, the control unit 30 responds to a selection of radiography requiring the second active configuration by controlling the flat panel sensor 32f to operate in the second active configuration, that is, so that the flat panel sensor 32f is configured with a one-dimensional linear sensor-like sensitive surface 32h to detect radiation emitted by the source 21 (FIG. 7b).

After the receiving device 22 is placed in the second active configuration, the operator operates the device 1 so as to perform the radiography procedure and acquire images of at least a part of the patient. For example, a scanning radiography procedure may be performed, as coordinated by control unit 30, by translating the gantry 20 by way of translation mechanism 53 while causing source 21 to emit radiation and detecting the radiation at the receiving device 22 after the radiation has traversed the patient, as described in U.S. patent application Ser. No. 14/323,808, entitled "RADIOLOGICAL IMAGING DEVICE WITH ADVANCED SENSORS," by Stoutenburgh et al., which is incorporated by reference herein in its entirety. Accordingly, high-resolution x-ray images are provided by operating the radiological imaging device 1 to perform a radiography procedure.

When the analysis of Step S812 is complete, the operator may perform additional imaging procedures (e.g., radiography, tomography, or fluoroscopy) by repeating Step S812 for the desired additional imaging procedures.

When the operator has completed all desired analyses in Step S812, the process ends at Step S814.

In view of the foregoing description, it can be appreciated that at least some example embodiments described herein provide a radiological imaging device 1 that can be used to perform computerized tomography, fluoroscopy and radiography in a single device.

In particular, owing to the presence of the receiving device 22 having the first detector 24, the second detector 25, and the movement apparatus 26, or in the alternative, the receiving device 22 having the flat panel sensor 32f capable of operating by selection in a matrix mode or a linear mode, the type of radiological imaging procedure performed by the device 1 can be changed in a fast manner.

Furthermore, high-quality tomography, fluoroscopy and radiography can be carried out in a radiological imaging device comprising a receiving device 22 that employs a flat panel sensor 24b with a sensitive surface 24a as a first detector 24 and at least linear sensor 25b with a sensitive surface(s) 25a as a second detector 25 owing to the fact that the distance between source 21 and the sensitive surface 24a in the first active configuration is substantially the same as the distance between the source 21 and the sensitive surface 25a in the second active configuration by virtue of the innovative movement apparatus 26. Similarly, when the radiological imaging device 1 comprises a receiving device 22 that employs a flat panel sensor 32f capable of operating in multiple independent modes, selectable by control unit 30, including at least a matrix mode (FIG. 7a) and a linear sensor mode (FIG. 7b), the distance between the source 21 and the sensitive surface 32g is substantially the same as the distance between the source 21 and the sensitive surface 32h, owing to the fact that both the first and the second active configurations are carried out on the same flat panel sensor 32f.

Additionally, the radiological imaging device 1 can perform different analyses on the patient without having to move said patient, and, as a consequence, risks associated with such maneuvers may be reduced or substantially minimized.

The device 1 can also perform radiological imaging procedures at a reduced cost owing to the fact that the radiological imaging device 1 is provided with different detectors 24 and 25.

Such a cost reduction is further enhanced by the fact that, maintaining the distance between the sensitive surfaces 24a and 25a and the source 21 constant permits the use of a structurally simpler source 21 which is economical, since it does not require the use of specific adjustment mechanisms to regulate the emission power according to the distance.

Moreover, a further reduction in costs can be achieved by virtue of the movement apparatus 26 which, by making it possible to change the active configuration of the radiological imaging device 1 quickly, permits analyses to be performed at a faster rate.

In addition, since it is possible to select the most suitable detector 24 and 25 for each analysis, the device 1 makes it possible to limit, or substantially reduce or minimize, exposure to X-rays.

An innovative radiological imaging procedure also is provided by virtue of to the radiological imaging device 1. With the radiological imaging procedure, the analysis can be performed when the patient is in the ideal condition, thus limiting exposure to radiation and the costs of the analysis. In particular, in the case of injecting a contrast liquid, the radiological imaging procedure allows the analysis to be performed when the liquid is in the portion of the body to be analyzed, thus avoiding the risk of a poor quality analysis due to the absence of the liquid in the portion to be analyzed. In at least some other cases, when the correct position of the patient is deemed important, by being able to check the position of the portion to be analyzed before performing the radiological imaging procedure, the radiological imaging procedure is only performed when the patient is in the desired position.

Additionally, by virtue of the radiological imaging device, the procedure can be carried out without moving the patient during the entire procedure.

Modifications and variations may be made to the example embodiments described herein without departing from the scope of the inventive concept. All the elements as described and claimed herein may be replaced with equivalent elements and the scope of the example embodiments includes all other details, materials, shapes and dimensions.

In addition, it should be understood that the attached drawings, which highlight functionality described herein, are presented as illustrative examples. The architecture of the present invention is sufficiently flexible and configurable, such that it can be utilized (and navigated) in ways other than that shown in the drawings.

Further, the purpose of the appended Abstract is to enable the U.S. Patent and Trademark Office and the public generally, and especially scientists, engineers, and practitioners in the relevant art(s), who are not familiar with patent or legal terms and/or phraseology, to determine quickly from a cursory inspection the nature and essence of the technical subject matter disclosed herein. The Abstract is not intended to be limiting as to the scope of the present invention in any way.

What is claimed is:

1. A radiological imaging device comprising:
   a source that emits x-ray radiation that passes through at least part of a patient, the x-ray radiation defining a central axis of propagation; and
   a receiving device that receives the x-ray radiation and is arranged on the opposite side of the patient with respect to the source,
   wherein the receiving device includes
      a first detector defining a first sensitive surface to detect x-ray radiation when performing at least one of tomography and fluoroscopy;
      a second detector defining a second sensitive surface to detect x-ray radiation when performing at least one of radiography and tomography; and
      a movement apparatus arranged to displace the first and second detectors with respect to the source, to provide a first active configuration in which the x-ray radiation hits the first detector and not the second detector, and a second active configuration in which the x-ray radiation hits the second detector and not the first detector, and in the first active configuration the first and second detectors are not directly attached to a common substrate;
   wherein the first detector comprises at least one flat panel sensor and the second detector comprises at least one linear sensor;
   wherein, in the first active configuration, the distance between the first detector and the source is substantially equal to the distance between the second detector and the source in the second active configuration;
   wherein the movement apparatus displaces the first and second detectors with respect to the source by means of a rotation about an axis of rotation;
   wherein the axis of rotation is substantially perpendicular to the central axis of propagation.

2. The radiological imaging device according to claim 1, wherein the movement apparatus changes between the first and second active configurations by means of a mutual translation of the first and second detectors.

3. The radiological imaging device according to claim 2, wherein the movement apparatus comprises a first linear actuator to move the first detector along a first direction of translation and a second linear actuator to move the second detector along a second direction of translation.

4. The radiological imaging device according to claim 3, wherein the first direction of translation is substantially perpendicular to the central axis of propagation and the second direction of translation is substantially parallel to the central axis of propagation.

5. The radiological imaging device according to claim 1, wherein the movement apparatus changes between the first and second active configurations by means of a translation of the first detector and a rotation of the second detector.

6. The radiological imaging device according to claim 1, wherein in the second active configuration the first and second sensitive surfaces are substantially coplanar.

7. The radiological imaging device according to claim 1, further comprising:
   a gantry defining an analysis zone in which the at least part of the patient is placed;
   a bed suitable to support the patient and defining an axis of extension;
   a translation mechanism adapted to translate the source and the receiving device in a direction of movement substantially perpendicular to the central axis of propagation;
   a rotation mechanism adapted to rotate the source and the receiving device in relation to the axis of extension;
   at least one positioning laser mounted on the gantry that projects a positioning guidance marker onto the patient;
   a control unit adapted to configure, based on received information, at least one of an energy of the x-ray radiation and a radiation filter arranged to absorb at least a portion of the x-ray radiation before the x-ray radiation passes through the at least part of the patient; and
   a diaphragm suitable to shape the x-ray radiation into at least one of a cone beam or a fan beam.

* * * * *

UNITED STATES PATENT AND TRADEMARK OFFICE
CERTIFICATE OF CORRECTION

Page 1 of 1

PATENT NO. : 10,265,042 B2
APPLICATION NO. : 14/323861
DATED : April 23, 2019
INVENTOR(S) : Gregory William Stoutenburgh et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 60 days.

Signed and Sealed this
Sixth Day of December, 2022

Katherine Kelly Vidal
*Director of the United States Patent and Trademark Office*